(12) United States Patent
Pusey et al.

(10) Patent No.: US 8,840,635 B2
(45) Date of Patent: Sep. 23, 2014

(54) LANCETS WITH IMPROVED COUPLING FEATURES AND STERILITY CAPS

(71) Applicant: Facet Technologies, LLC, Kennesaw, GA (US)

(72) Inventors: Lauren R. Pusey, Woodstock, GA (US); Brian M. Collins, Denver, CO (US); Christopher J. Ruf, Marietta, GA (US); Nicholas H. Reaves, Atlanta, GA (US); Jonathan W. Sanders, Portage, MI (US)

(73) Assignee: Facet Technologies, LLC, Kennesaw, GA (US)

( * ) Notice: Subject to any disclaimer, the term of this patent is extended or adjusted under 35 U.S.C. 154(b) by 0 days.

(21) Appl. No.: 13/675,209

(22) Filed: Nov. 13, 2012

(65) Prior Publication Data
US 2013/0072953 A1  Mar. 21, 2013

Related U.S. Application Data

(62) Division of application No. 13/293,409, filed on Nov. 10, 2011, which is a division of application No. 12/510,701, filed on Jul. 28, 2009, now abandoned.

(60) Provisional application No. 61/084,456, filed on Jul. 29, 2008.

(51) Int. Cl.
*A61B 17/14*  (2006.01)

(52) U.S. Cl.
USPC ......................................... 606/182

(58) Field of Classification Search
CPC ................ A61B 17/32093; A61B 5/1411
USPC ................ 606/181, 182; 600/573, 583
See application file for complete search history.

(56) References Cited

U.S. PATENT DOCUMENTS

| | | | |
|---|---|---|---|
| 2,839,056 A | 6/1958 | Mailly | |
| 3,358,689 A | 12/1967 | Higgins | |
| 3,680,559 A * | 8/1972 | Gorbahn | 604/193 |
| 4,577,630 A | 3/1986 | Nitzsche et al. | |
| 4,858,607 A | 8/1989 | Jordan et al. | |

(Continued)

FOREIGN PATENT DOCUMENTS

| | | |
|---|---|---|
| EP | 0595148 A1 | 5/1994 |
| EP | 0747006 A1 | 12/1996 |

(Continued)

OTHER PUBLICATIONS

Anhui Kangda (Shanghai Care Life), Thin Lancets; date unknown; 2 pgs.

(Continued)

*Primary Examiner* — Victor Nguyen
(74) *Attorney, Agent, or Firm* — Gardner Groff Greenwald & Villanueva, PC

(57) ABSTRACT

Improved lancet configurations and protective lancet endcap configurations are disclosed. In example forms, one or more flexing cantilevers project from the lancet body for coupling with a cooperating receiver of a lancing device. A gripping handle extends from a sterility cap for ease of removal from and replacement over the lancet tip. A lancet body has a smoothly curved wave contour with at least one crest and at least one trough for engagement with a cooperating receiver of a lancing device.

18 Claims, 9 Drawing Sheets

(56) References Cited

U.S. PATENT DOCUMENTS

| | | | |
|---|---|---|---|
| 4,889,117 | A | 12/1989 | Stevens |
| 4,990,154 | A | 2/1991 | Brown et al. |
| 4,994,068 | A * | 2/1991 | Hufnagle ..................... 606/181 |
| 5,314,442 | A | 5/1994 | Morita |
| 5,324,303 | A | 6/1994 | Strong et al. |
| 5,385,571 | A | 1/1995 | Morita |
| 5,454,828 | A | 10/1995 | Schraga |
| 5,569,286 | A | 10/1996 | Peckham et al. |
| 5,755,733 | A * | 5/1998 | Morita .......................... 606/182 |
| 5,868,772 | A | 2/1999 | LeVaughn et al. |
| D445,183 | S | 7/2001 | McWethy et al. |
| 6,299,626 | B1 | 10/2001 | Viranyi |
| 6,322,574 | B1 | 11/2001 | Lloyd et al. |
| 6,589,261 | B1 | 7/2003 | Abulhaj et al. |
| D484,244 | S | 12/2003 | Starnes |
| 6,723,111 | B2 | 4/2004 | Abulhaj et al. |
| D493,527 | S | 7/2004 | Szabo |
| 6,945,982 | B2 | 9/2005 | Marshall et al. |
| D533,943 | S | 12/2006 | Chen |
| 7,150,755 | B2 | 12/2006 | LeVaughn et al. |
| D535,397 | S | 1/2007 | Chen |
| D562,980 | S | 2/2008 | Marshall |
| D567,944 | S | 4/2008 | Sarna |
| 7,357,808 | B2 | 4/2008 | Kennedy |
| D570,478 | S | 6/2008 | Sudo |
| D581,046 | S | 11/2008 | Sudo |
| D586,465 | S | 2/2009 | Faulkner et al. |
| D586,916 | S | 2/2009 | Faulkner et al. |
| 7,655,017 | B2 | 2/2010 | Starnes |
| 7,670,301 | B2 | 3/2010 | Roe |
| 7,955,347 | B2 | 6/2011 | Stout |
| 7,955,348 | B2 | 6/2011 | Trissel et al. |
| 2003/0109895 | A1 | 6/2003 | Taylor et al. |
| 2004/0059365 | A1 | 3/2004 | Abulhaj et al. |
| 2006/0052809 | A1 | 3/2006 | Karbowniczek et al. |
| 2007/0083222 | A1 | 4/2007 | Schraga |

FOREIGN PATENT DOCUMENTS

| | | |
|---|---|---|
| EP | 0589186 B1 | 11/1999 |
| EP | 1285629 A1 | 2/2003 |
| EP | 1929949 A1 | 6/2008 |
| WO | 0128423 A2 | 4/2001 |
| WO | 2007097283 A1 | 8/2007 |
| WO | 2007130830 A2 | 11/2007 |
| WO | 2009006461 A1 | 1/2009 |
| WO | 2009015097 A2 | 1/2009 |

OTHER PUBLICATIONS

Asahi Polyslider, Abbott Thin Lancets; date unknown; 3 pgs.
Asahi Polyslider, Arkray Multilet Lancet; date unknown; 2 pgs.
Asahi Polyslider, Facet Technologies (Gainor Medical) Cleanlet 25G; date unknown; 2 pgs.
International Search Report and Written Opinion for PCT/US20069/051943; Feb. 17, 2010; 18 pgs.
Owen Mumford, Unilet ComforTouch; date unknown; 2 pgs.
Owen Mumford, Unilet ExceLite; date unknown; 2 pgs.
Owen Mumford, Unilet GP Superlite; date unknown; 2 pgs.
Partial International Search Report for PCT/US2009/051943; Nov. 16, 2009; 7 pgs.

* cited by examiner

LANCETS WITH IMPROVED COUPLING FEATURES AND STERILITY CAPS

CROSS-REFERENCE TO RELATED APPLICATION

This application is a divisional of U.S. Non-Provisional patent application Ser. No. 13/293,409 filed Nov. 10, 2011, which is a divisional of U.S. Non-Provisional patent application Ser. No. 12/510,701 filed Jul. 28, 2009, which claims the benefit of U.S. Provisional Patent Application Ser. No. 61/084,456 filed Jul. 29, 2008, the entireties of which are hereby incorporated herein by reference for all purposes.

TECHNICAL FIELD

The present invention relates generally to the field of medical devices, and more particularly to lancets and lancing devices for blood sampling and testing.

BACKGROUND OF THE INVENTION

Lancets and lancing devices are utilized for penetrating the skin of a human or animal subject at a lancing site to obtain a sample of blood or other body fluid for medical testing, as in blood-typing or blood-glucose testing. Known lancing devices commonly include a housing containing a drive mechanism, a charging mechanism for energizing the spring or other drive means of the drive mechanism, and a release mechanism for releasing the drive mechanism upon actuation. A lancet is typically propelled by the drive mechanism from a retracted position shielded within the housing to an extended position wherein a sharp tip portion of the lancet projects from the housing to prick the subject's skin at a desired lancing site. An ejection mechanism can optionally be included for discharge of a used lancet from the lancing device.

The lancet is typically a disposable component that is removably mounted into a receiver or lancet carrier portion of the drive mechanism of a lancing device. A used lancet typically is removed from the lancet carrier after sampling for disposal. A new, sterile lancet is then replaced into the lancet carrier for further sampling. Lancets typically comprise a sharp metal tip in the form of a needle or blade. The needle or blade is typically embedded in a plastic body that has a size and shape configured for releasable engagement with the receiver or lancet carrier of a lancing device. The sharp tip of the lancet is commonly embedded in a removable plastic cap to maintain sterility and prevent inadvertent sticks prior to use. The endcap may be replaceable onto the lancet after use to re-cover the sharp lancet tip for safety and hygienic purposes.

It is to the provision of improved lancets that the present invention is primarily directed.

SUMMARY OF THE INVENTION

In example embodiments, the present invention provides improved lancet designs with various advantages over previously known lancets. In one aspect, the present invention relates to a lancet having one or more cantilevers or resilient coupling members, such as arms, fingers, barbs, flared portions, projections, or the like on the lancet body, for engagement with a cooperating coupling member of a lancing device, facilitating ease of insertion and ejection in use.

In another aspect, the present invention relates to a lancet having a sterility cap or protective cover with a handle or grip portion for assisting in removal of the cap for use of the lancet and/or for replacement of the cap onto a used lancet for disposal.

In still another aspect, the present invention relates to a sterility cap or protective cover for a lancet, the cap or cover having a handle for assisting in removal of the cap from the lancet, and/or for replacement of the cap onto a used lancet for disposal.

In another aspect, the present invention relates to a lancet having a lancet body with a smoothly curved side profile, having at least one crest and at least one trough for engagement with cooperating coupling portions of a lancing device. An expanded disc or flange optionally projects from the lancet body to assist in ejection and removal of the lancet.

In another aspect, the invention relates to a lancet comprising a lancet body, a sharp lancing tip projecting from a first end of the lancet body, and at least one resilient coupling member for releasable engagement with a cooperating coupling member of a lancing device.

In yet another aspect, the invention relates to a protective sterility cap for a lancet, the sterility cap comprising a primary sheath for initial embedment of a sharp lancing tip of an unused lancet therein, and a gripping handle portion extending from the primary sheath.

In another aspect, the invention relates to a lancet system including a lancet having a lancet body and a sharp lancing tip projecting from the lancet body, wherein the lancet body comprises at least one resilient coupling member and defines a lancet body thickness. The lancet system further includes an endcap having a primary shroud portion initially surrounding the sharp lancing tip of the lancet, a secondary shroud portion for placement over the sharp lancing tip of the lancet after use, and a handle portion extending between the primary shroud portion and the secondary shroud portion.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

DETAILED DESCRIPTION OF EXAMPLE EMBODIMENTS

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "an" "and" "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, such as by use of the antecedent "approximately" or "about," it will be understood that the particular value forms another embodiment.

Figure 1A:
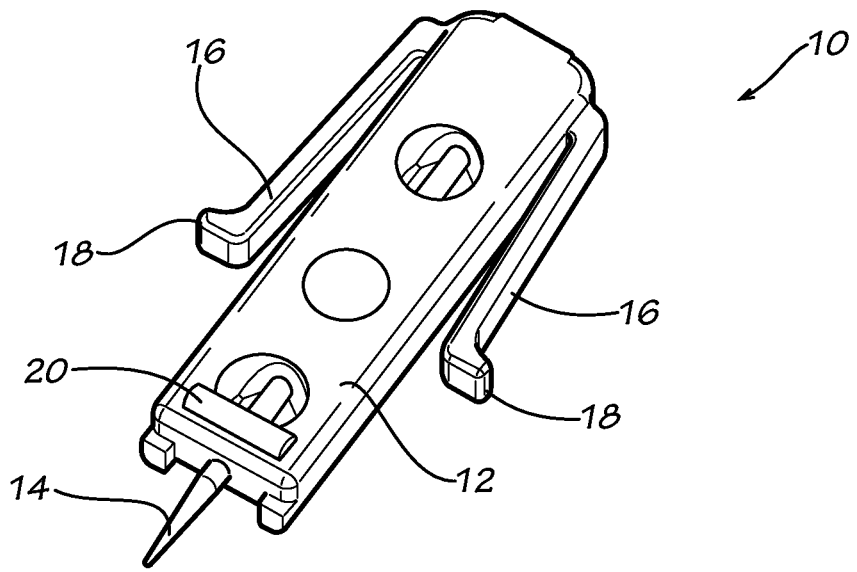
FIGS. 1A-1C show an example embodiment of a lancet according to one form of the invention.
Figure 1B:
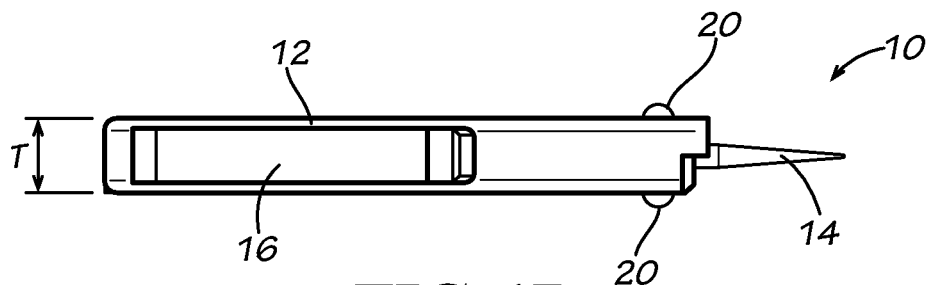
Figure 1C:
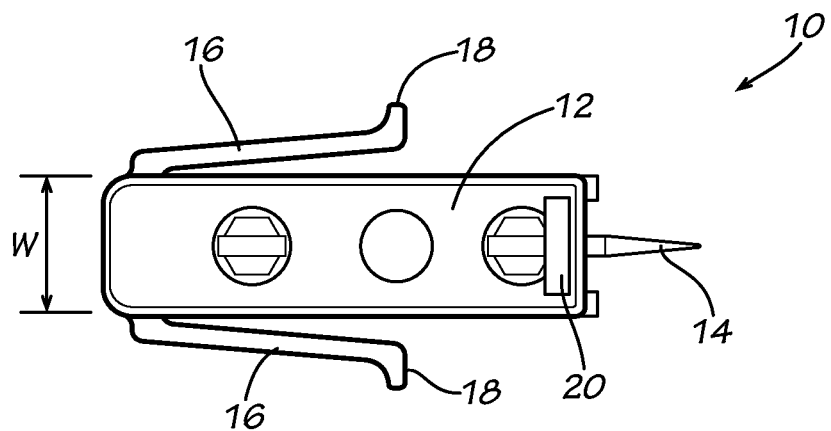

With reference now to the drawing figures, FIGS. 1A-1C show a lancet 10 according to an example form of the invention. The lancet 10 includes a body portion 12 having a sharp lancet tip 14 projecting from a front or first end thereof, and one or more (two are depicted) resilient coupling members in the form of cantilevered fingers 16 projecting from sides of the body portion. The cantilevered fingers 16 have a base end connected proximal to the back or second end of the body portion, and a free end projecting outwardly and toward the front of the body portion. The cantilevered fingers 16 preferably taper outwardly from their base end toward their free end, thereby defining a smoothly tapered lead-in profile adjacent the back end of the lancet body for easier alignment during installation into a lancing device for use. The free end of each cantilevered finger optionally comprises a shoulder or barb 18 extending laterally outward relative to the longitudinal axis of the lancet body 12. One or more ribs or protrusions 20 optionally project outwardly from upper and lower faces of the lancet body for engagement with an ejection member of the lancet to discharge a used lancet from the lancing device. The lancet body has a thickness T and a width W, with the width W preferably being at least about 1.5 times, and more preferably at least about twice the thickness T, thereby reducing potential twisting and misalignment of the lancet within the receiver of the lancing device during installation.

In use, the lancet 10 is installed into the receiver or lancet carrier of a lancing device by inserting the rear end into the receiver and pressing it axially into the lancet carrier. The cantilevered fingers 16 flex inwardly upon contact with cooperating portions of the receiver. The taper of the cantilevered fingers 16 provides guidance of the lancet during installation. As the lancet reaches its fully engaged position within the receiver, the cantilevered fingers 16 spring outwardly under their own resilience, and the shoulders or barbs 18 snap into engagement with cooperating portions of the receiver to positively engage the lancet carrier. Optionally, audible or tactile feedback indicates proper engagement of the lancet within the lancet carrier to the user. The cantilevered fingers 16 optionally also provide an interface between the lancet and the lancing device for ejection, wherein an ejection mechanism flexes the fingers inwardly and releases the lancet from the lancet carrier.

Figure 2A:
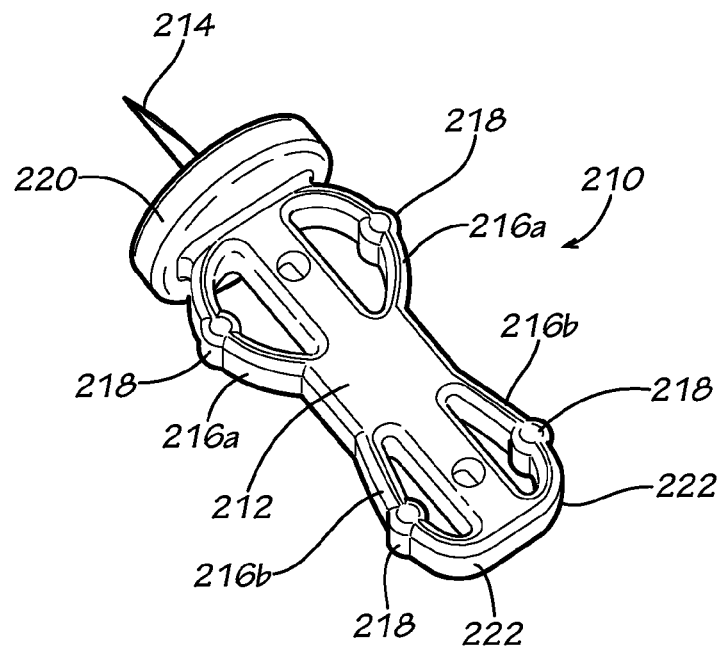
FIGS. 2A-2C show an example embodiment of a lancet according to another form of the invention.
Figure 2B:
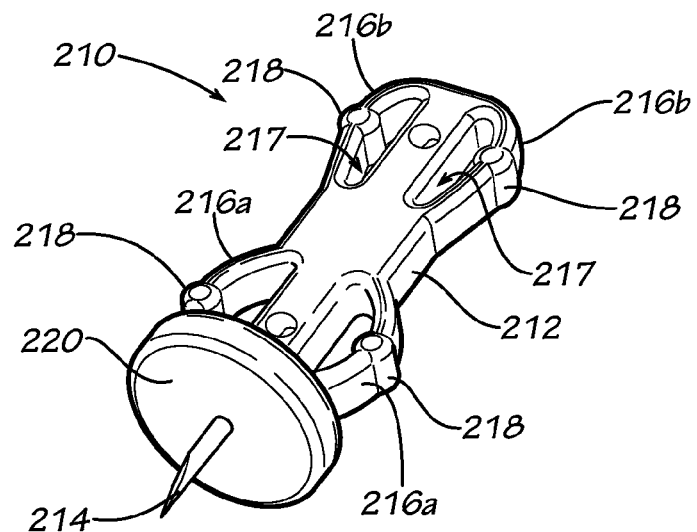
Figure 2C:
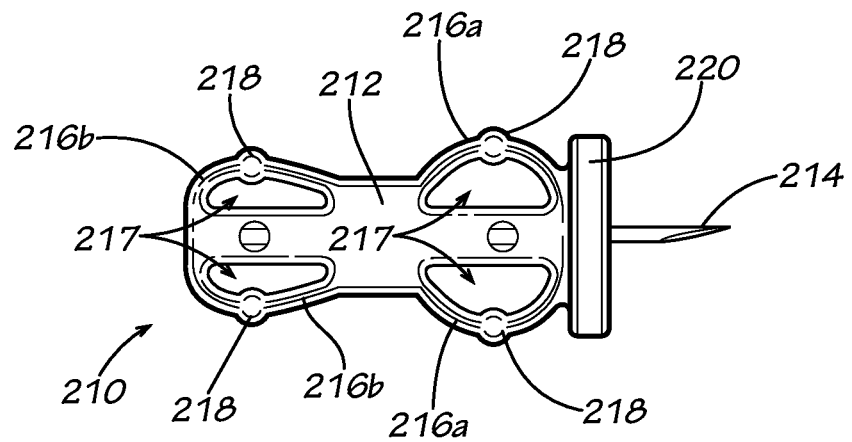
Figure 3A:
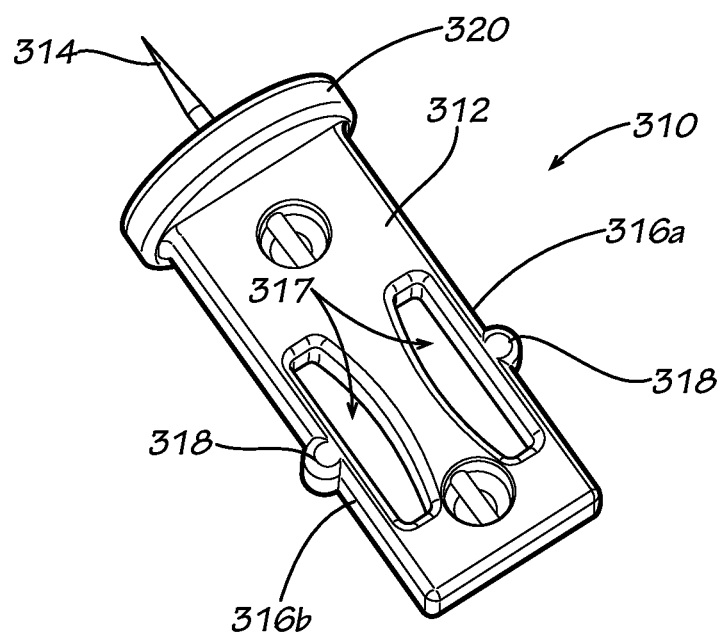
FIGS. 3A-3D show an example embodiment of a lancet according to another form of the invention.
Figure 3B:
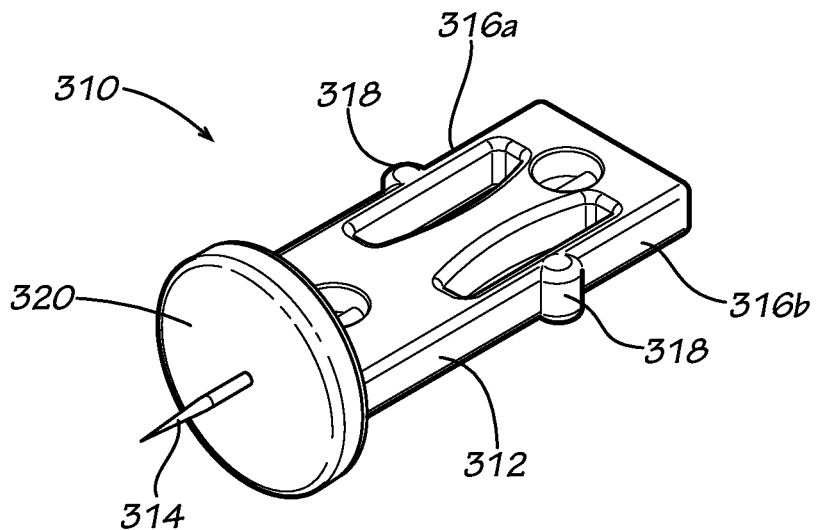
Figure 3C:
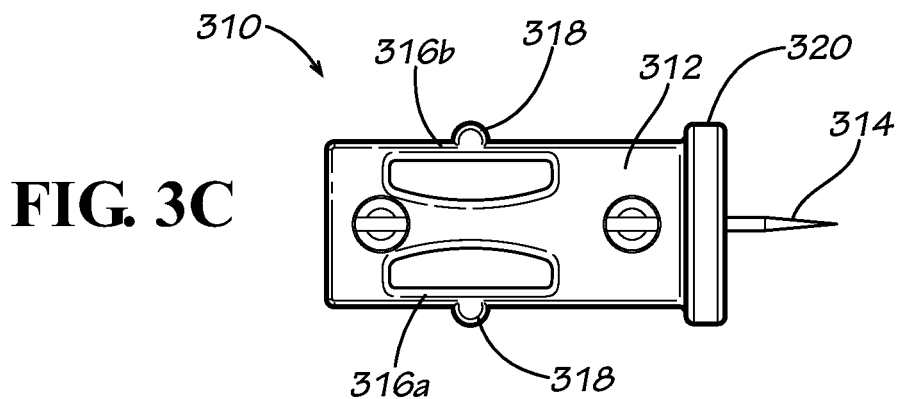
Figure 3D:
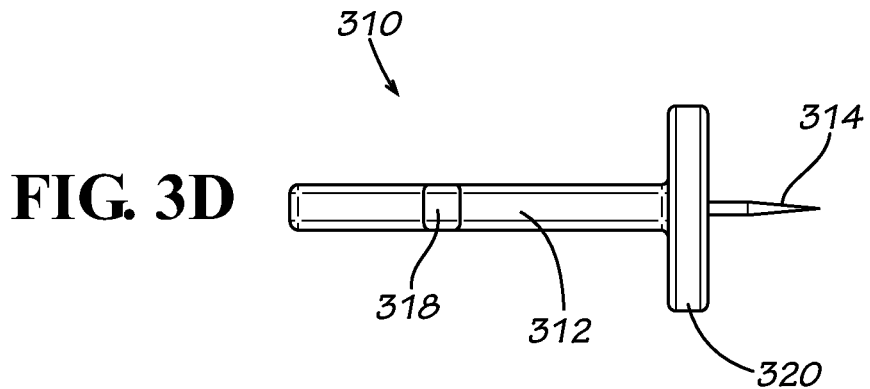
Figure 4A:
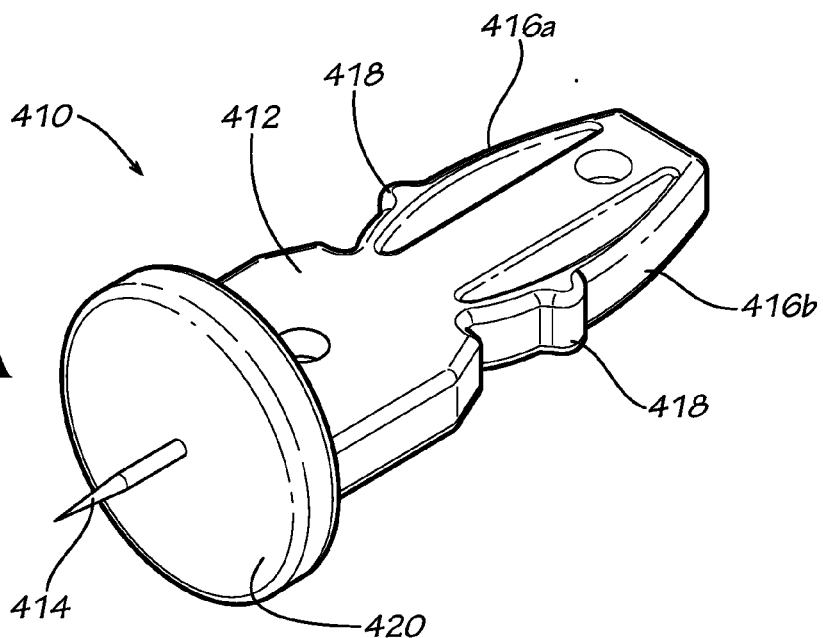
FIGS. 4A-4D show an example embodiment of a lancet according to another form of the invention.
Figure 4B:
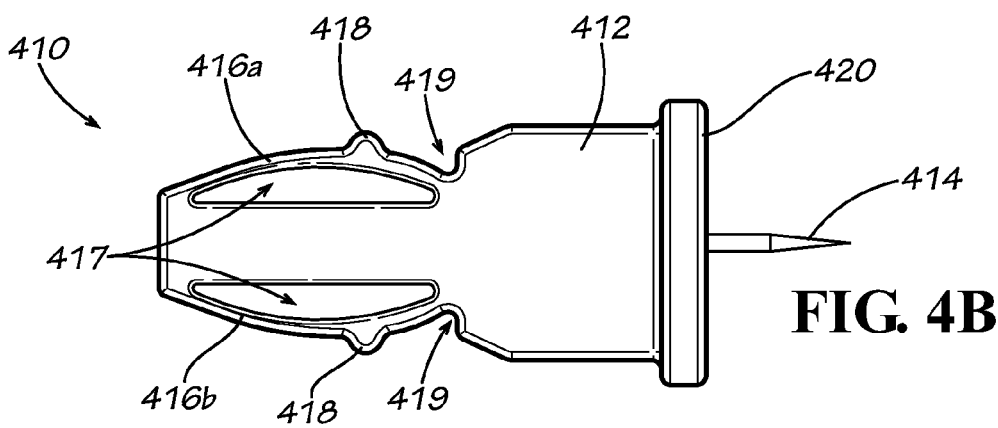
Figure 4C:
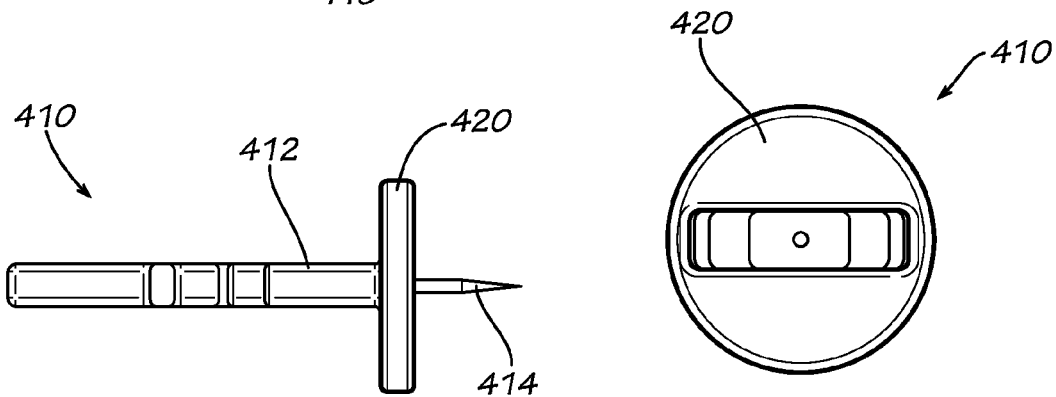
Figure 4D:
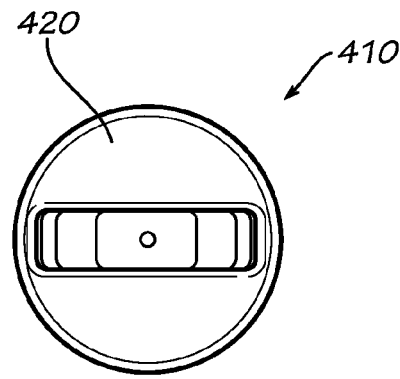
Figure 5A:
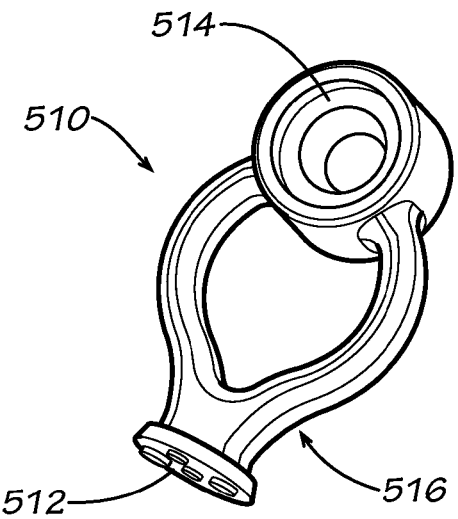
FIGS. 5A-5E show an example embodiment of an endcap for a lancet according to one form of the invention.
Figure 5B:
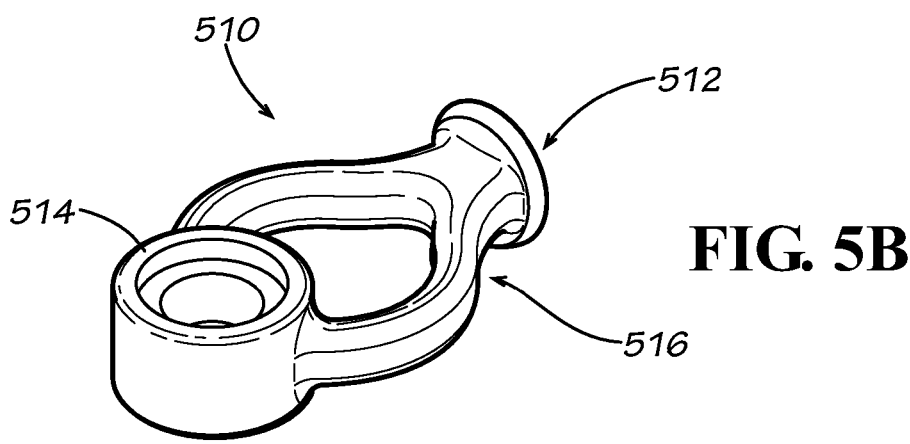
Figure 5C:
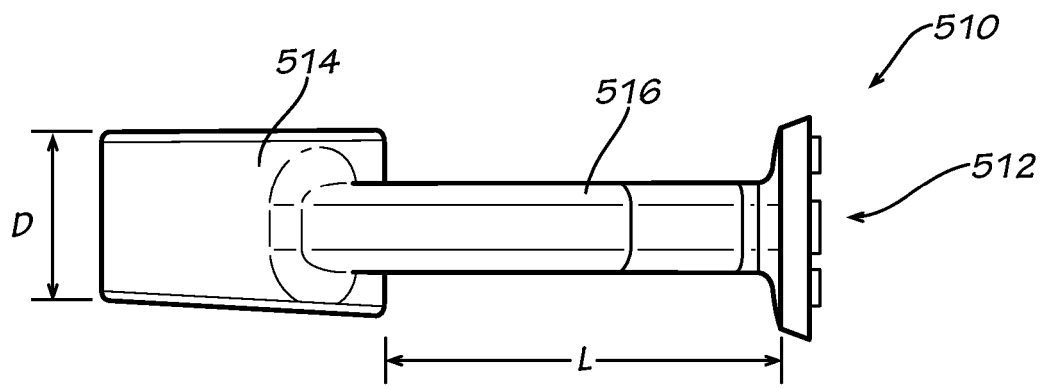
Figure 5D:
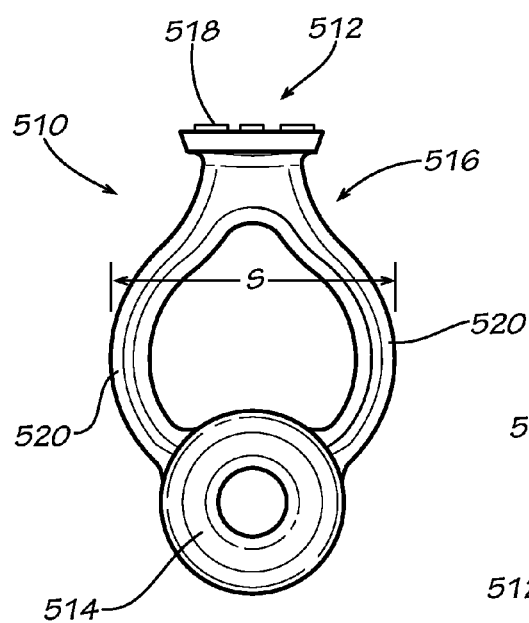
Figure 5E:
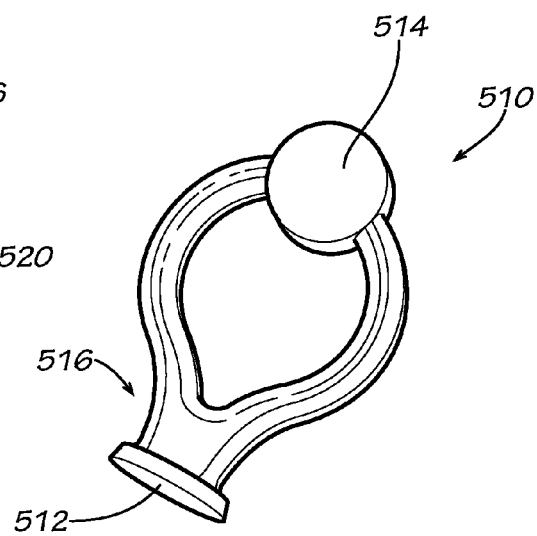
Figure 6A:
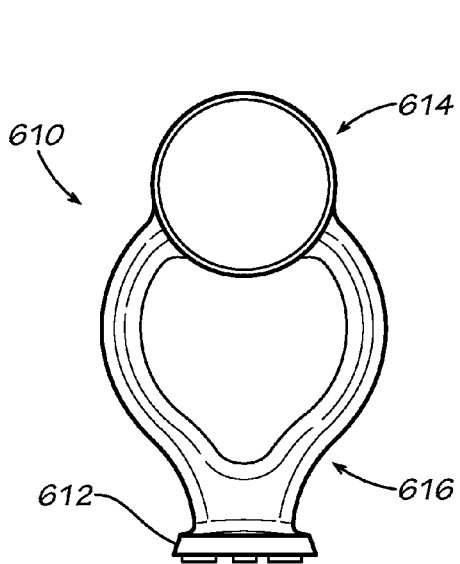
FIGS. 6A-6D show an example embodiment of an endcap for a lancet according to another form of the invention.
Figure 6B:
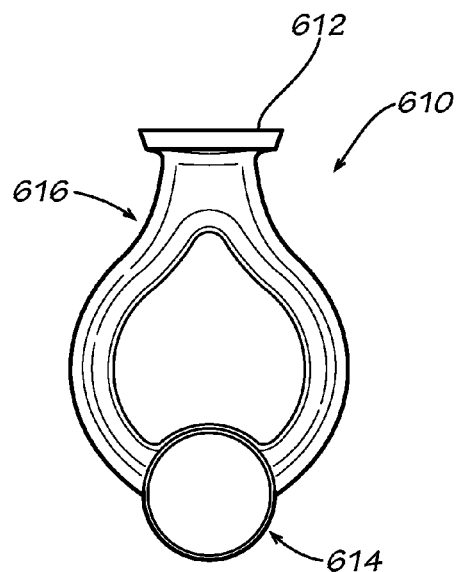
Figure 6C:
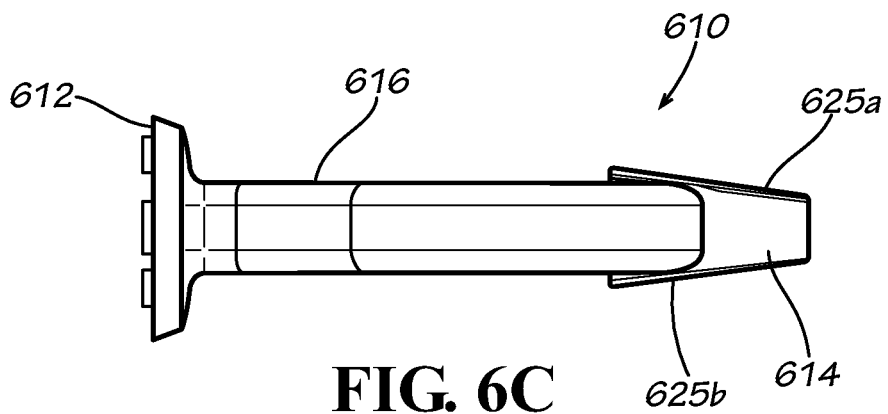
Figure 6D:
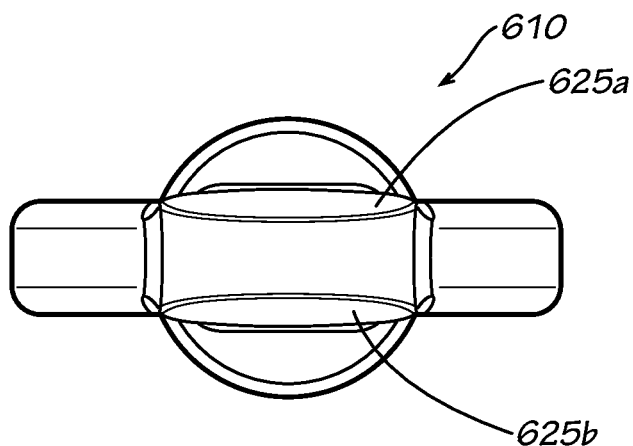

FIGS. 2A-2C show a lancet 210 according to another example form of the invention. The lancet 210 includes a body portion 212 having a sharp lancet tip 214 projecting from a front or first end thereof, and one or more resilient coupling members in the form of flexible arches or loops 216a, 216b projecting outwardly from sides of the body portion and surrounding open hollows or cutout portions 217 of the lancet body portion 212. The flexible arches or loops are arranged in two opposed pairs, a larger forward pair 216a and a smaller rearward pair 216b, thereby defining an overall body profile tapering from wider at the forward end to narrower at the rearward end, and having a convex inward recess at a medial portion between the forward and rearward pairs of flexible loops. In example embodiments, the maximum width of the lancet body portion at the rearward pair of flexible loops (undeformed) is at least about 1.1 times the minimum width at the inward recess of the medial portion, and the maximum width of the lancet body portion at the forward pair of flexible loops (undeformed) is at least about 1.2 times the minimum width at the inward recess of the medial portion. Each of the flexible arches or loops 216a, 216b optionally includes a shoulder or knob 218 at its outermost portion for positive engagement with a cooperating portion of the receiver of a lancing device. A flange or ring 220 is optionally provided extending transversly outward around at least a portion of the periphery of the front end of the lancet body 212 to provide an interface for lancet removal, either manually or by an ejection mechanism of the lancing device. The transitions 222 between the rear end of the lancet body and the sides of the lancet body optionally form a smoothly contoured arcuate or rounded profile, for guidance and ease of installation of the lancet into a lancing device.

FIGS. 3A-3D show a lancet 310 according to another example form of the invention. The lancet 310 includes a body portion 312 having a sharp lancet tip 314 projecting from a front or first end thereof, and one or more (one opposed pair is depicted) resilient coupling members in the form of flexible panels or body portions 316a, 316b projecting outwardly from sides of the body portion. Each of the flexible panels or body portions 316a, 316b optionally includes a bulb or knob 318 at its outermost portion for positive engagement with a cooperating portion of the receiver of a lancing device. The body 312 of the lancet defines a generally rectangular profile, having substantially flat or planar upper and lower faces and sides, with the outer faces of the flexible panels 316a, 316b forming generally continuous segments of the flat sides of the body 312 bounding open hollows or cutout portions 317 of the lancet body portion 312. The cutouts 317 preferably have a transverse dimension equal or greater than the outward projection of the knob 318. A flange or ring 320 is optionally provided extending transversly outward around at least a portion of the periphery of the front end of the lancet body 312 to provide an interface for lancet removal, either manually or by an ejection mechanism of the lancing device.

FIGS. 4A-4D show a lancet 410 according to another example form of the invention. The lancet 410 includes a body portion 412 having a sharp lancet tip 414 projecting from a front or first end thereof, and one or more (one opposed pair is depicted) resilient coupling members in the form of flexible arches or loops 416a, 416b projecting outwardly from sides of the body portion and enclosing open hollows or cutout portions 417 of the lancet body portion 412. The flexible arches or loops 416a, 416b have first and second ends connected to the lancet body and medial portions between the first and second ends separated a distance from the lancet body to define the open hollows 417 therebetween. The flexible arches or loops 416a, 416b are positioned adjacent the rear end of the body portion 412 of the lancet, with their distal ends forming a smoothly curving or arcuate lead-in portion for guidance and ease of insertion and removal of the lancet from the receiver of a lancing device. Each of the flexible arches or loops 416a, 416b optionally includes an outwardly projecting bulb or knob 418 at its outermost portion for positive engagement with a cooperating portion of the receiver of a lancing device. An inwardly directed recess 419 is defined at the forward extent of the loops 416, along the lateral sides of the lancet body. A flange or ring 420 is optionally provided, extending transversly outward around at least a portion of the periphery of the front end of the lancet body 412 to provide an interface for lancet removal, either manually or by an ejection mechanism of the lancing device.

The flexibility of the opposed resilient coupling members arranged symmetrically on either side of the lancet body in the various embodiments "absorbs" tolerances in dimensions of the lancet and the cooperating receiver of the lancing device, automatically adjusting the fit and alignment of the lancet to the lancing device and providing smoother installation and removal of the lancet to and from the lancing device. Imprecise alignment of the lancet in the lancet carrier may result in increased pain sensation by the subject. Thus, by maintaining proper alignment of the lancet within the lancing device, with the lancet tip moving substantially entirely axially along the lancing stroke, with little or no transverse wobble, rotation or twisting movement, the lancet of the present invention may result in a lower-pain lancing procedure, potentially improving compliance with a prescribed testing regimen.

The improved design of the lancet of the present invention also readily allows adjustment of the forces required for insertion and removal of the lancet to and from the lancing device, by selective variation of the material stiffness, thickness, and/or location of the resilient coupling members. The tapered shape of the lancet body aids in installation and ejection of the lancet. Also, the tapered body contour and positive engagement features provided by the resilient coupling members enable a shorter lancet ejection stroke of the ejection mechanism of a lancing device, as the lancet is more rapidly disengaged by inward flexure of the resilient coupling members than many previously known lancet designs utilizing friction engagement of the lancet within the receiver of the lancing device.

The lancet of the present invention further enables the provision of a more simplified lancet receiver or carrier in a cooperating lancing device. The various forms of lancet designs according to the present invention allow a unique or proprietary matching lancet and lancet receiver or carrier, whereby only lancets of the specified design will fit and engage within the receiver or carrier of a corresponding lancing device. In this manner, the user can be assured of the type and/or source of the lancet being used, including its quality, sterility, size, format and/or other characteristics. Additionally, the positive engagement mechanism of the resilient coupling members within the lancet carrier reduce the chances of partial or incomplete insertion of the lancet into the lancing device, as the lancets may be configured to click or snap into position notifying the user of complete insertion.

FIGS. 5A-5E show a protective/sterility cap or cover 510 for a lancet according to an example form of the present invention. The cap or cover 510 includes a first or primary shroud or sheath portion 512 for receiving and protecting the sharp tip of a lancet in its initial or unused state, a secondary shroud or sheath portion 514 for receiving and protecting the sharp tip of a lancet in its final or used state, and a "handle" or extension arm portion 516 extending between the primary and secondary shrouds for assisting in removal of the cap from the lancet, and/or for replacement of the cap onto a used lancet for disposal. The handles allow for the body of the lancet to be smaller than a Regular Version (RV) lancet, allowing the corresponding lancing devices to be smaller. The sterility caps optionally have one or more readily visible circular or flat areas that can be used for applying branding/logos, and are positioned so that the user can replace the cap by inserting the exposed sharp of the lancet therein before disposal.

The primary shroud or sheath portion 512 comprises a wide circular flange or ring at one end of the sterility cap 510, which abuts, confronts or interfaces with the front end of the lancet body in the lancet's original, unused state. In example forms of the invention, the sterility cap 510 is integrally molded with the lancet body. One or more spacer ribs or breakaway connections 518 are optionally provided, extending from the primary shroud or sheath portion 512 to the front end of the lancet body. Intact spacer ribs or breakaway connections 518 indicate an unused lancet, whereas broken spacer ribs or breakaway connections 518 indicate the lancet may have been used and therefore may not be sterile. The wide circular flange or ring of the primary shroud or sheath portion 512 may also assist in lancet insertion into the lancing device, providing a hard stop against a cooperating portion of the lancing device for consistent placement, and/or providing a surface against which the user presses during installation.

The secondary shroud or sheath portion 514 comprises a cup having an outer rim and a hollow interior chamber. When sharp lancet tip of the lancet is placed into the secondary shroud or sheath portion 514 after use of the lancet, the lancet tip is received within the hollow interior chamber of the cup, and protected from inadvertent contact by the outer rim. One or more retainers or couplings are optionally provided within the cup of the secondary shroud or sheath portion 514 for engagement with cooperating portions of the lancet body to retain the sterility cap 510 in place on the lancet. The secondary shroud or sheath portion 514 has a depth D greater than the length of the exposed portion of the lancet tip extending beyond the lancet body to prevent the lancet tip from extending through the secondary shroud or sheath portion.

The handle or extension arm portion 516 defines a forked or split configuration having first and second arms 520 transversely spaced apart from one another, with an open center portion therebetween. This forked arrangement provides the handle with a greater width, allowing the user to more easily twist the endcap during removal from the lancet. In example forms, the lateral or transverse span S of the forked handle portion 516 is at least about 1.5 times, and more preferably at least about 2 times the diameter or thickness of the lancet body. In example forms, the length L of the handle portion is at least equal to the span S, and/or is greater than the depth D of the secondary shroud 514, and/or is greater than the diameter or thickness of the lancet body. The provision of the elongate handle portion 516 allows the user to grab the lancet further from the needle during decapping and disposal, providing a larger safety margin from the needle tip, protecting the patient and other persons handling the lancet from accidental needle sticks. Additionally, the expanded dimensions of the endcap allow for easier use by persons with limited dexterity or vision, and permit the use of smaller lancets with lower mass and/or finer gauge needles, which may reduce pain.

FIGS. 6A-6D show a protective/sterility cap or cover 610 for a lancet according to another example form of the present invention. The cap or cover 610 includes a first or primary shroud or sheath portion 612 for receiving and protecting the sharp tip of a lancet in its initial or unused state, a secondary shroud or sheath portion 614 for receiving and protecting the sharp tip of a lancet in its final or used state, and a "handle" or extension arm portion 616 extending between the primary and secondary shrouds. The secondary shroud or sheath portion 614 comprises a disc having tapered flat panels 625a, 625b on either side for embedding the sharp lancet tip therein. Optionally, the disc having tapered flat panels serves as a gripping portion of the handle and/or as a display surface only, and not as a shroud or sheath for the needle, in which case the needle is replaced into the first or primary shroud or sheath portion after use.

Figure 7:
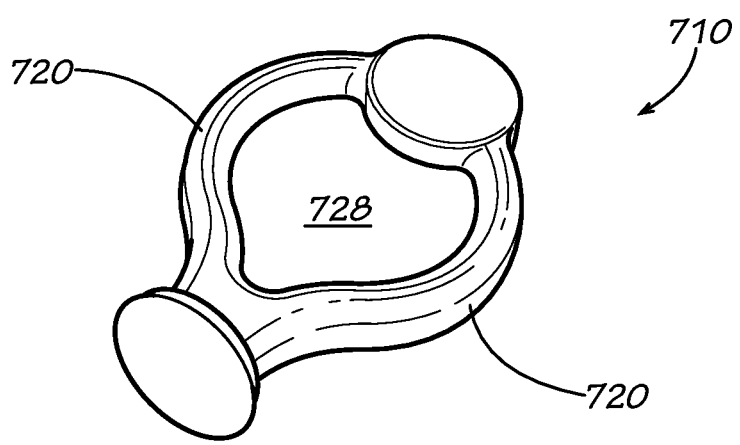
FIG. 7 shows an example embodiment of an endcap for a lancet according to another form of the invention.
Figure 8A:
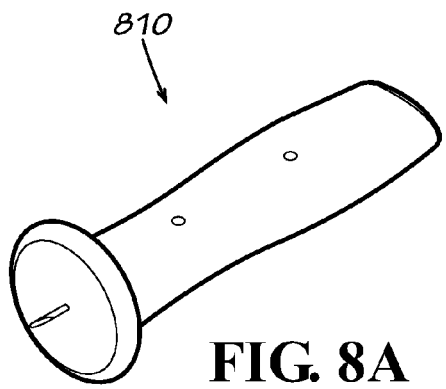
FIGS. 8A and 8B show an example embodiment of a lancet according to another form of the invention.
Figure 8B:
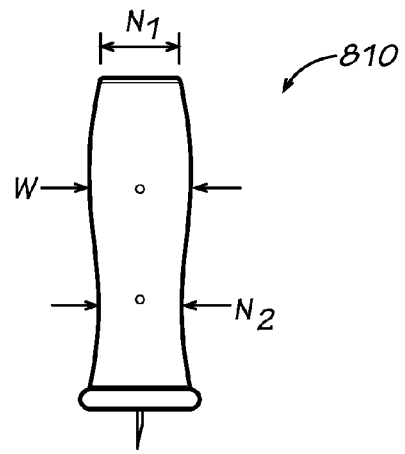
Figure 9A:
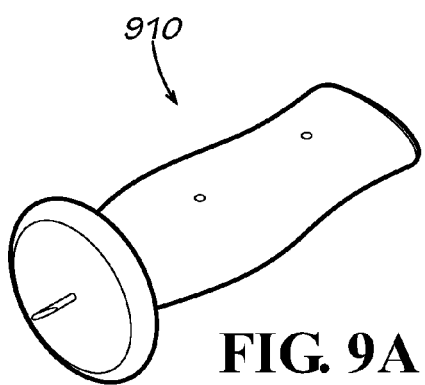
FIGS. 9A and 9B show an example embodiment of a lancet according to another form of the invention.
Figure 9B:
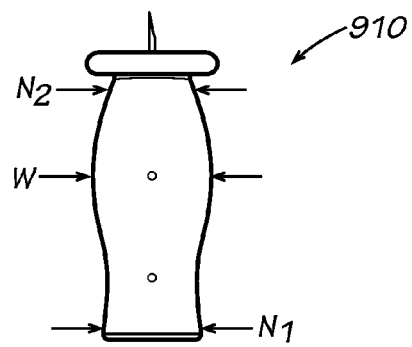
Figure 10A:
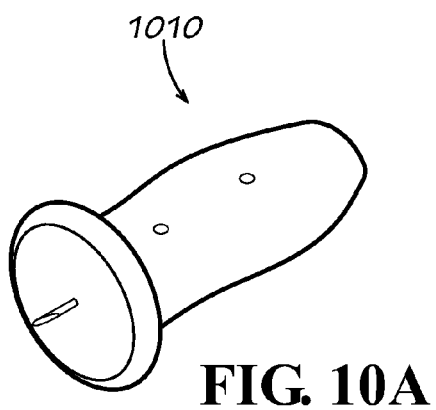
FIGS. 10A and 10B show an example embodiment of a lancet according to another form of the invention.
Figure 10B:
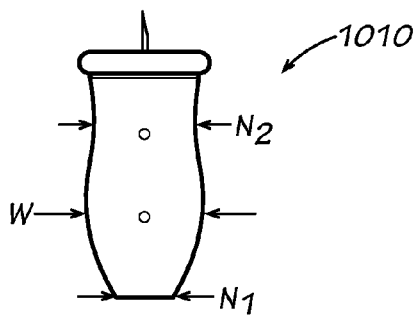

FIG. 7 shows a protective/sterility cap or cover 710 substantially similar to the above-described forms, but having a thin solid panel 728 extending between the first and second arms 720 of the handle portion, which may reduce the likelihood of tangling of lancets within a package during shipping and storage.

The protective/sterility cap or cover provides an intuitive modality for users to grab when handling a lancet. Additionally, the larger surface area provided by the protective/sterility cap, as compared to previously known designs, makes it easier to locate, especially for users with reduced visual acuity; and renders it easier to pick up off of a flat surface or out of a container, which is particularly advantageous for users with reduced manual dexterity.

FIGS. 8A and 8B, 9A and 9B, and 10A and 10B show lancets 810, 910 and 1010, respectively, according to additional forms of the invention. These lancets include a lancet body that allows for the lancet to be inserted into the device and snapped into position. Each of these variations includes a lancet body with a wave-shaped or concave/convex peripheral profile, with a first narrower dimension $N_1$ proximal the rear end of the lancet, a wider dimension W around the middle of the lancet, and a second narrower dimension $N_2$ toward the forward end. In example forms, the wider dimension W is at least about 1.1 times, and optionally at least about 1.2 times, the lesser of the narrower dimensions $N_1$ or $N_2$. The lancet body is optionally generally flattened, having a width that is substantially greater than its thickness, in example forms having an aspect ratio of the width relative to the thickness of at least about 3:2. The wavy design of the lancet body is shaped so that it snaps into engagement with a cooperating coupling of the lancing device at the narrower section N of the lancet body and/or fits snugly at the wider section W and is easy to eject due to the smooth curves and transitions on the lancet body.

The lancet body can be formed of a resilient material and/or the receiver of the lancing device can comprise a resilient coupling for releasable engagement therebetween. Optionally, the lancet body comprises one or more hollow chambers or cutout portions for additional flexure and deformation in coupling with the lancing device. The lancet body design also is curvy and appealing to the user, preferably having a smoothly contoured outer lancet body profile without sharp corners, which may appear less intimidating to a user and more "friendly" and "painless," thereby reducing the appearance or perception to the user of being a lancet that causes pain. The smooth shape of the lancet provides positive tactile feedback, and does not have any sharp edges to remind the user of a regular lancet. The curved design is easy to pick up off of many different surfaces, and the disc at the front of the lancet allows for easier grip for manual removal from the lancing device and can be used of lancet ejection. Troughs on the lancet body allow for attachment areas that interact with the lancing device to hold the lancet in place, and crests on the lancet body allow for press fit/friction fit of the lancet into the lancing device. The positioning and configuration of these attachment points on the lancet allow for shorter ejection strokes for lancet removal.

The present invention also encompasses a lancet system comprising a lancet according to any of the forms disclosed herein, in combination with a protective sterility cap according to any of the forms disclosed herein. In its original unused state, the lancet system is configured with the sharp lancet tip of the lancet embedded in the primary shroud or sheath portion of the sterility cap. The user installs the lancet into a corresponding lancing device by gripping the lancet system by the handle portion of the cap and inserting the back end of the lancet into the receiver of the lancing device until the resilient coupling members positively engage with cooperating engagement portions the receiver. The endcap is then removed, as for example by twisting and pulling the shroud off of the lancet tip. After use, the endcap may be replaced to cover the sharp lancet tip by embedding or enclosing the lancet tip into the secondary shroud or sheath portion of the endcap.

While the invention has been described with reference to preferred and example embodiments, it will be understood by those skilled in the art that a variety of modifications, additions and deletions are within the scope of the invention, as defined by the following claims.

What is claimed is:

1. A protective sterility cap for a lancet, said sterility cap comprising a primary sheath for initial embedment of a sharp lancing tip of an unused lancet therein, a secondary sheath for receiving the sharp lancing tip of a used lancet, and a gripping handle portion extending between the primary sheath and the secondary sheath, with the primary sheath attached at a first end of the gripping handle portion and the secondary sheath attached at a second end of the gripping handle portion when the protective sterility cap is removed from the lancet.

2. The protective sterility cap of claim 1, in combination with a lancet.

3. The protective sterility cap of claim 1, further comprising at least one flat display surface for placement of branding indicia thereon.

4. The protective sterility cap of claim 1, wherein the gripping handle portion comprises at least one open loop.

5. The protective sterility cap of claim 1, wherein the gripping handle portion comprises a solid body without an open loop.

6. The protective sterility cap of claim 1, in combination with a lancet having a lancet body defining a lancet thickness, and a sharp lancet tip initially embedded in the primary sheath, wherein the gripping handle portion defines a lateral span of at least 1.5 times the lancet thickness.

7. The protective sterility cap of claim 6, wherein the gripping handle portion defines a length at least equal to its lateral span.

8. The protective sterility cap of claim 6, wherein the gripping handle portion defines a length at least equal to the lancet thickness.

9. A protective sterility cap for a lancet, said sterility cap comprising a primary sheath for initial embedment of a sharp lancing tip of an unused lancet therein, a secondary sheath for receiving the sharp lancing tip of a used lancet, and a gripping handle portion extending between the primary sheath and the secondary sheath, with the primary sheath attached at a first end of the gripping handle portion and the secondary sheath attached at a second end of the gripping handle portion when the protective sterility cap is removed from the lancet, and wherein the gripping handle portion comprises at least one open loop.

10. The protective sterility cap of claim 9, further comprising at least one flat display surface for placement of branding indicia thereon.

11. The protective sterility cap of claim 9, in combination with a lancet having a lancet body defining a lancet thickness, and a sharp lancet tip initially embedded in the primary sheath, wherein the gripping handle portion defines a lateral span of at least 1.5 times the lancet thickness.

12. The protective sterility cap of claim 11, wherein the gripping handle portion defines a length at least equal to its lateral span.

13. The protective sterility cap of claim 11, wherein the gripping handle portion defines a length at least equal to the lancet thickness.

14. A protective sterility cap for a lancet, said sterility cap comprising a primary sheath for initial embedment of a sharp lancing tip of an unused lancet therein, a secondary sheath for receiving the sharp lancing tip of a used lancet, and a gripping handle portion extending between the primary sheath and the secondary sheath, with the primary sheath attached at a first end of the gripping handle portion and the secondary sheath attached at a second end of the gripping handle portion when the protective sterility cap is removed from the lancet, said protective sterility cap being in combination with a lancet having a lancet body defining a lancet thickness, and a sharp lancet tip initially embedded in the primary sheath, wherein the gripping handle portion defines a lateral span of at least 1.5 times the lancet thickness.

15. The protective sterility cap of claim 14, wherein the gripping handle portion comprises at least one open loop.

16. The protective sterility cap of claim 14, further comprising at least one flat display surface for placement of branding indicia thereon.

17. The protective sterility cap of claim 14, wherein the gripping handle portion defines a length at least equal to its lateral span.

18. The protective sterility cap of claim 14, wherein the gripping handle portion defines a length at least equal to the lancet thickness.

* * * * *